US010912879B2

(12) United States Patent
Orwig

(10) Patent No.: US 10,912,879 B2
(45) Date of Patent: Feb. 9, 2021

(54) COLLECTION DEVICE FOR USE IN IRRIGATION AND DRAINAGE PROCEDURES

(71) Applicant: Drue Maureen Orwig, Ada, MI (US)

(72) Inventor: Drue Maureen Orwig, Ada, MI (US)

(*) Notice: Subject to any disclaimer, the term of this patent is extended or adjusted under 35 U.S.C. 154(b) by 507 days.

(21) Appl. No.: 15/782,984

(22) Filed: Oct. 13, 2017

(65) Prior Publication Data
US 2018/0104405 A1  Apr. 19, 2018

Related U.S. Application Data

(60) Provisional application No. 62/407,602, filed on Oct. 13, 2016.

(51) Int. Cl.
*A61M 3/02* (2006.01)
*A61M 1/00* (2006.01)

(52) U.S. Cl.
CPC ........ *A61M 3/0287* (2013.01); *A61M 1/0019* (2013.01); *A61M 1/0021* (2013.01); *A61M 1/0058* (2013.01); *A61M 1/0084* (2013.01); *A61M 3/0233* (2013.01)

(58) Field of Classification Search
CPC ............ A61F 5/44; A61F 5/4404–4408; A61F 5/442; A61F 2013/00536; A61M 3/0287
USPC ................. 604/351–353, 355, 356
See application file for complete search history.

(56) References Cited

U.S. PATENT DOCUMENTS

| | | | | |
|---|---|---|---|---|
| 3,199,507 A | * | 8/1965 | Kamm | A61G 7/02 600/575 |
| 3,288,140 A | * | 11/1966 | McCarthy | A61H 35/00 604/289 |
| 3,910,274 A | * | 10/1975 | Nolan | A61F 5/442 604/277 |
| 4,270,539 A | * | 6/1981 | Frosch | A61F 5/455 4/144.3 |
| 4,376,437 A | * | 3/1983 | Sundheim | A61M 35/30 602/2 |
| 4,994,051 A | * | 2/1991 | Walsh | A61F 5/453 604/349 |
| 5,002,069 A | * | 3/1991 | Thompson | A61B 46/00 128/849 |
| 5,107,859 A | * | 4/1992 | Alcorn | A61F 5/445 128/849 |
| 5,178,162 A | * | 1/1993 | Bose | A61B 46/27 128/849 |
| 5,248,307 A | * | 9/1993 | Sokoloff | A61M 27/00 128/846 |

(Continued)

FOREIGN PATENT DOCUMENTS

| | | |
|---|---|---|
| CN | 203898812 U | 10/2014 |
| EP | 0355186 A1 | 2/1990 |
| WO | 2016054470 A1 | 4/2016 |

OTHER PUBLICATIONS

Polypropylene (PP), AMCOPolymers.com, 2019 (Year: 2019).*

*Primary Examiner* — Susan S Su
(74) *Attorney, Agent, or Firm* — Price Heneveld LLP

(57) ABSTRACT

A fluid collection device includes an upper edge portion having a first end of a collection container having an outer surface where the upper edge portion defines an open top end. At least one fastening device may be attached to the outer surface of the collection container. A vacuum hose coupled to an outlet port extends from a second end of the collection container. A vacuum source applies a vacuum to the collection container through the vacuum hose.

20 Claims, 8 Drawing Sheets

(56) References Cited

U.S. PATENT DOCUMENTS

| | | | | |
|---|---|---|---|---|
| 5,312,385 A * | 5/1994 | Greco | A61H 35/00 128/DIG. 24 |
| 5,370,637 A * | 12/1994 | Brodeur | A61F 5/4556 4/144.3 |
| 5,624,419 A * | 4/1997 | Ersek | A61M 3/0262 604/304 |
| 5,735,835 A * | 4/1998 | Holland | A61F 5/455 604/327 |
| 5,911,222 A * | 6/1999 | Lawrence | A61F 5/455 600/573 |
| 5,941,859 A * | 8/1999 | Lerman | A61M 27/00 604/289 |
| 6,050,981 A | 4/2000 | Lampropoulos et al. | |
| 6,402,724 B1 | 6/2002 | Smith et al. | |
| 6,562,013 B1 * | 5/2003 | Marasco, Jr. | A61M 3/022 604/290 |
| 6,635,035 B1 * | 10/2003 | Marasco | A61M 35/30 604/290 |
| 7,520,872 B2 | 4/2009 | Biggie et al. | |
| 7,543,587 B2 * | 6/2009 | Yardan | A61B 46/20 128/849 |
| 7,678,092 B2 * | 3/2010 | Matloub | A61M 1/008 604/355 |
| 7,976,522 B2 * | 7/2011 | Hansen | A61F 5/4404 604/338 |
| 8,491,548 B2 | 7/2013 | Livne et al. | |
| 8,636,178 B2 * | 1/2014 | McGinley | A45D 19/00 220/609 |
| 8,657,796 B2 | 2/2014 | Marasco | |
| 8,968,262 B2 * | 3/2015 | Tapadiya | A61B 50/30 604/356 |
| 2001/0037098 A1 * | 11/2001 | Snyder | A61F 5/4553 604/331 |
| 2002/0193760 A1 * | 12/2002 | Thompson | A61F 5/4556 604/318 |
| 2004/0060566 A1 * | 4/2004 | Musso | A61B 46/00 128/849 |
| 2008/0219642 A1 * | 9/2008 | Matloub | A61F 13/00038 386/241 |
| 2010/0137820 A1 * | 6/2010 | Lee | A61B 46/00 604/322 |
| 2011/0015560 A1 * | 1/2011 | Marasco | A61M 1/0088 604/20 |
| 2013/0211425 A1 * | 8/2013 | Parsell | A61B 17/3203 606/131 |
| 2015/0359660 A1 * | 12/2015 | Harvie | A61F 5/4404 604/351 |
| 2016/0242867 A1 * | 8/2016 | Davison | A61M 1/0088 |

* cited by examiner

COLLECTION DEVICE FOR USE IN IRRIGATION AND DRAINAGE PROCEDURES

CROSS-REFERENCE TO RELATED APPLICATION

This application claims priority under 35 U.S.C. § 119(e) to U.S. Provisional Patent Application No. 62/407,602, filed Oct. 13, 2016, entitled "COLLECTION DEVICE FOR USE IN IRRIGATION AND DRAINAGE PROCEDURES," which is herein incorporated by reference in its entirety.

FIELD OF THE INVENTION

The present disclosure generally relates to a wound irrigation/fluid collection system that is connected to a patient for cleaning of a wound or incision.

BACKGROUND OF THE INVENTION

The cleaning and washing of wounds or incisions is typically required to remove foreign material and to decrease bacterial contamination. When washing a wound, a wound care provider, first responder, nurse, physician, or surgeon should be protected or isolated from any bodily fluids and/or contaminated irrigation fluids.

Typically, a collection pan or receptacle is placed under the wound that is to be treated in order to collect the irrigation fluid used during the irrigation and debridement. Debridement is the removal of foreign matter such as dirt, contaminants, or dead tissue. Irrigation is the flushing of fluid over the wound to remove smaller particles and bacteria to decrease the possibility of infection.

During irrigation and debridement procedures, it may be difficult to trap all of the irrigation fluid with a bulky collection pan. Further, in many instances, the irrigation fluid can splash onto the wound care provider, equipment, and/or surroundings. In other words, the collection pan placed under the wound usually does not catch all of the irrigation or wound fluids that are present during the irrigation and debridement procedure. These circumstances are of particular concern when the patient has blood borne pathogens such as HIV or hepatitis, thereby putting the wound care provider at risk of contracting an infectious disease. When a patient may not be aware that they have contracted an infectious disease, the adoption of universal precautions has been recommended. The spillage of contaminated irrigation fluid requires sterilization of the materials in the immediate environment, which could include carpeting, walls, bed coverings, and/or clothing.

Therefore, there is a need in the art for a fluid collection system that can provide a barrier for health care providers for splash or spillage of contaminated irrigation fluids or bodily fluids.

SUMMARY OF THE INVENTION

According to one aspect of the present disclosure, a fluid collection device includes a upper edge portion coupled to a first end of a collection container having an outer surface wherein the upper edge portion defines an open top end; at least one adhesive surface coupled to the outer surface of the collection container; and a second end of the collection container having an outlet port, wherein the outlet port is adapted to be placed in communication with a vacuum source.

According to another aspect of the present disclosure, a fluid collection device includes a collection container having an upper edge portion positioned at a first end where the upper edge portion defines an open top end; a lip and a ridge coupled to the upper edge portion; and a second end of the collection container having an outlet port. The lip can be formed to a shape of a patient's body directly below a laceration and the ridge is configured to couple a fastener to hold the fluid collection device to the patient's body.

According to yet another aspect of the present disclosure, a method for irrigating and draining a laceration includes steps of: applying a fluid collection device directly below the laceration. The fluid collection device has an upper edge portion coupled to a first end of a collection container having an outer surface wherein the upper edge portion defines an open top end; at least one adhesive surface coupled to the outer surface of the collection container; and a second end defining an outlet port connecting a vacuum source to the outlet port to define a vacuum region proximate the upper edge portion and around the laceration. The method for irrigating and draining a laceration further includes irrigating and/or debriding the laceration with a fluid to remove dirt, contaminates, and/or dead tissue; and collecting the fluid with the fluid collection device.

According to still another aspect of the present disclosure, a method for making a fluid collection device includes steps of: coupling a upper edge portion to a first end of a collection container having an outer surface wherein the upper edge portion defines an open top end; coupling at least one adhesive surface to the outer surface of the collection container; and coupling an outlet port to a second end of the collection container, wherein the outlet port is a rigid member that partially maintains the collection bag in an open configuration to place an area defined by the upper edge portion in communication with the outlet port.

These and other features, advantages, and objects of the present invention will be further understood and appreciated by those skilled in the art by reference to the following specification, claims, and appended drawings.

DETAILED DESCRIPTION

Figure 1:
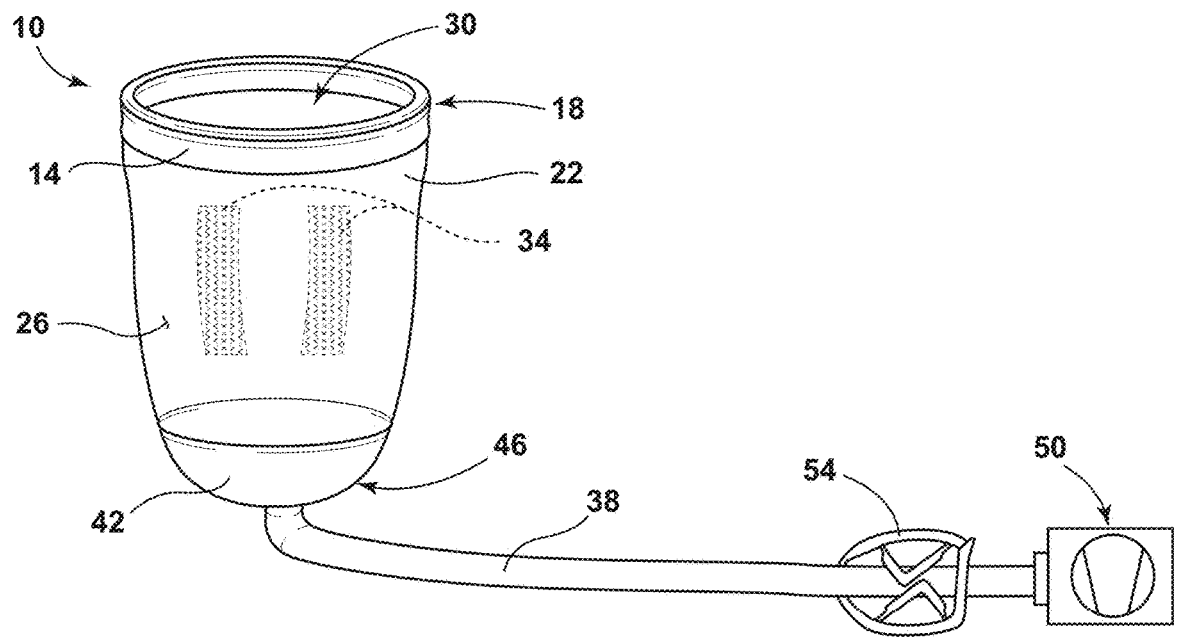
FIG. 1 is a rear isometric view of a fluid collection device according to one aspect of the current invention.

Additional features and advantages of the invention will be set forth in the detailed description which follows and will be apparent to those skilled in the art from the description or recognized by practicing the invention as described in the following description together with the claims and appended drawings.

As used herein, the term "and/or," wherein used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Referring now to FIGS. 1-5, reference numeral 10 generally designates a fluid collection device. The fluid collection device 10 includes an upper edge portion 14 having a first end 18 of a collection container 22 having an outer surface 26 where the upper edge portion 14 defines an open top end 30. At least one adhesive surface 34 may be attached to the outer surface 26 of the collection container 22. A second end 46 of the collection container 22 has an outlet port 42, wherein the outlet port 42 is placed in communication with a vacuum source 50.

The fluid collection device 10 may be used to improve patient care so that blood, bodily fluids, water, and/or other contaminated fluids do not flow all over a patient during procedures. For example, indications for using the fluid collection device 10 may include nosebleeds, surgical procedures, ear wax de-impactions, and/or the irrigation or debridement of lacerations, incisions, sores, or any other type of wound. As described below, in some aspects, the fluid collection device 10 may be assisted by vacuum-power, gravity, or a combination of both vacuum and gravity.

Referring now to FIG. 1, the fluid collection device 10 has the upper edge portion 14 coupled to the collection container 22 so that the open top end 30 is formed. The outer surface 26 of the collection container 22 may have at least one adhesive surface 34 attached. A vacuum hose 38 having a pinch clip 54 is coupled to the outlet port 42 which extends from the second end 46 of the collection container 22. The vacuum source 50 applies a vacuum 56 to an interior volume 58 of the collection container 22 through the vacuum hose 38. The pinch clip 54 may be used anywhere along the length of the vacuum hose 38 to either cut off or start applying the vacuum 56 to the interior volume 58 of the fluid collection device 10.

The upper edge portion 14 may be composed of a moldable shape resistant thermopolymer, a moldable rubber, or any other flexibly rigid material known in the art. In some embodiments, the upper edge portion 14 comprises a moldable shape resistant thermopolymer. In other embodiments, the upper edge portion 14 may have a piece of metal surrounded by a moldable shape resistant thermopolymer. The upper edge portion 14 may allow for medical staff to mold the upper edge portion 14 to substantially the same shape as the surface and contours of the patient's body 62. Depending on the desired application, manner for storing, and/or method of use, the upper edge portion 14 may be pliable, flexible, collapsible, stiff, hard, or rigid. In some embodiments, the upper edge portion 14 may be fabricated using the same material as the collection container 22.

Figure 4:
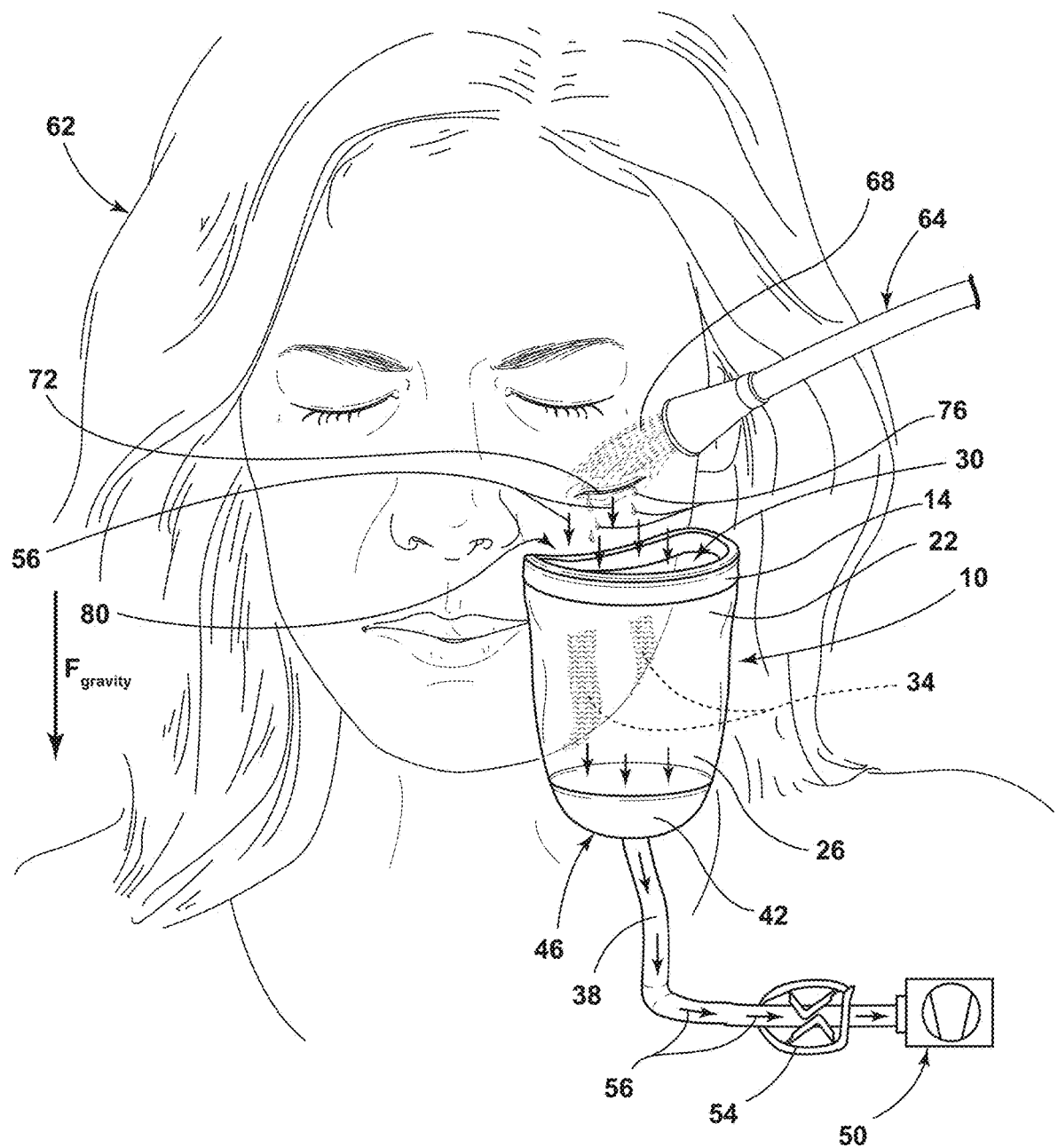
FIG. 4 is a front perspective view illustrating a spraying device and a fluid collection device attached to a patient's face.

The at least one adhesive surface 34 may be composed of one or more adhesive strips, a two-sided tape, a two-sided adhesive bandage, or any other adhesive material known in the art that could be used to connect the collection container 22 of the fluid collection device 10 to a patient's body 62 (see FIG. 4). In some embodiments, the adhesive surface 34 may be applied or coupled to the outer edge or surface of the upper edge portion 14 to connect the fluid collection device 10 to the patient's body 62. In other embodiments, the adhesive surface 34 may be applied or coupled to the collection container 22 and/or the outer edge or surface of the upper ring edge portion 14 to connect the fluid collection device 10 to the patient's body 62. In some instances, an additional fastening device such as an elastic band, gauze, tape, bandage, or film may be additionally coupled to the fluid collection device 10 to facilitate or assist in connection of the fluid collection device 10 to the patient's body 62. In some embodiments, the fluid collection device 10 may not have any adhesive surface 34 coupled to the collection container 22.

Figure 2:
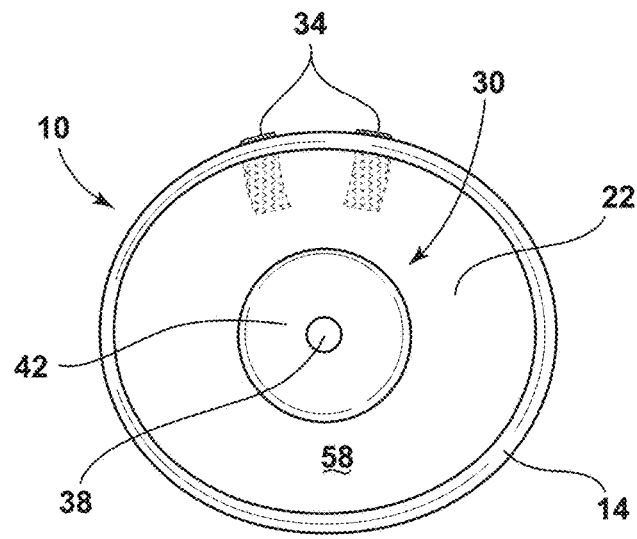
FIG. 2 is a top view of the fluid collection device shown in FIG. 1.

Referring now to FIG. 2, a top view of the fluid collection device 10 shows the at least one adhesive surface 34 coupled to and projecting away from the outer surface 26 (FIG. 1). The open top end 30 is formed by the upper edge portion 14 which leads down to the collection container 22 and further down to the outlet port 42. The vacuum hose 38 is coupled to the outlet port 42. An interior volume 58 is formed by the area enclosed with the upper edge portion 14, collection container 22, and outlet port 42. In some embodiments, the upper edge portion 14, collection container 22, and outlet port 42 may be cast or molded together to give a single molded piece making up the fluid collection device 10. In other embodiments, the upper edge portion 14, collection container 22, and outlet port 42 may each be detachable from one another to disassemble the fluid collection container 10.

Figure 3:
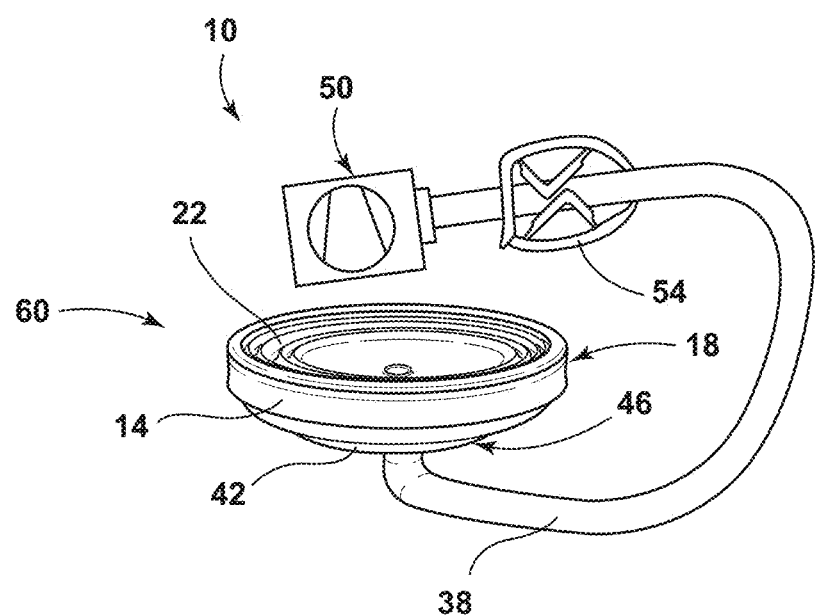
FIG. 3 is a side view of the collapsed fluid collection device of FIG. 1.

Referring now to FIG. 3, in some embodiments, the first end 18 and the second end 46 of the fluid collection device 10 may fold in towards each other to collapse into a compact structure 60 for storage and/or disposal. In a folded or collapsed state, the outlet port 42 can be positioned within the upper edge portion 14 where the coupled collection container 22 fills in the space and folds between and/or around the upper edge portion 14 and outlet port 42. The vacuum hose 38 and attached pinch clip 54 may be positioned anywhere around or in the compact structure 60. In some embodiments, the first end 18 and the second end 46 of the collection container 22 fold towards each other to collapse into the compact structure 60 to define a flat-storage position.

Referring now to FIG. 4, the fluid collection device 10 may be configured to be attached to the patient's body 62 below a laceration 72. A pressurized spraying device/means 64 may be separately used to project a fluid 68 onto and in the laceration 72 to irrigate and/or debride the laceration 72. Contaminated fluids 76 are produced once the spraying device 64 applies the fluid 68 into and around the laceration 72. The contaminated fluids 76 will flow downwards with respect to gravity ($F_{gravity}$) so that the contaminated fluids 76 flow into the open top end 30 formed by the upper edge portion 14 attached to the patient's body 62 beneath the laceration 72. As the contaminated fluids 76 flow down into the interior volume 58 of the collection container 22 and further down into the outlet port 42, the contaminated fluids 76 may be removed from the interior volume 58 through the application of vacuum 56 by the vacuum source 50 through the vacuum hose 38. At any time, the health care provider can cease or activate the applied vacuum 56 through the pinch clip 54. In some embodiments, the upper edge portion 14 can be formed to a shape of the patient's body 62 directly below the laceration 72. In other embodiments, the vacuum source 50 further defines a vacuum region 80 and selectively provides a suction force to assist in removal of the fluid 68 collected in the collection container 22 through the vacuum hose 38. The vacuum region 80 exists throughout the interior volume 58 of the fluid collection device 10 where the vacuum 56 is applied and extends to the area above the open top end 30 and adjacent to the laceration 72 to facilitate the collection of the fluid 68 and the contaminated fluids 76 into the fluid collection device 10. The vacuum region 80 assists in the collection of fluids 68, 76 without applying excessive suction to the laceration 72.

In some embodiments, the health care provider may detach the vacuum hose 38 from the outlet port 42 of the fluid collection device 10. Upon detaching the vacuum hose 38 from the vacuum adapter 42, the vacuum adapter 42 may be blocked with a cap 104 (FIG. 7) or a plug (not shown) to prevent the fluid 68 and/or the contaminated fluids 76 from flowing out. Removal of the vacuum hose 38 may be desired if no vacuum 56 is available or if minimal fluids 68 and/or contaminated fluids 76 are expected to be collected.

Administration of the fluid 68 to the laceration 72 is made possible through the device's pressurized spraying means 64. The streaming of the fluid 68 to irrigate and/or debride the laceration 72 effectively washes away secretions, exudates, debris, and bacteria while also maintaining a moist wound bed. The pressurized spraying means 64 may be used to enhance the laceration's 72 healing process and also to help protect the laceration 72 from pathogens and contaminants. In some embodiments, the pressurized spraying means 64 may be separately provided by a hospital or other provider.

The vacuum source 50 may be supplied by a number of different non-limiting options, for example, a hospital's house-vacuum system, a portable pump, or a battery-operated suction pump. The vacuum source 50 may apply the vacuum 56 or a negative pressure to the vacuum-powered, fluid collection device 10 varied over a range from atmospheric pressure to about 1 millimeter of mercury (mm/Hg). A typical negative pressure is approximately 125 mm/Hg below atmospheric pressure. The vacuum region 80 formed by the outlet port 42 being placed in communication with the vacuum source 50 may extend one or more inches above the open top end 30 depending on the strength of the vacuum 56 (negative pressure) applied.

The at least one adhesive surface 34 that is coupled to the outer surface 26 of the collection container 22 may be applied directly to the patient's body 62 below the laceration 72 to be irrigated or debrided. The upper edge portion 14 can be molded or formed to the shape of a patient's body 62 as required. The vacuum source 50 assists in the removal of the fluid 68 and contaminated fluids 76 collected in the interior volume 58 of the collection container 22 by applying the vacuum 56 through the vacuum hose 38. In some embodiments, the at least one adhesive surface 34 is coupled to a patient's body 62 directly below the laceration 72.

The collection container 22 facilitates collection and storage of the fluid 68 and contaminated fluids 76 collected through gravity and/or the vacuum source 50. In some embodiments, the collection container 22 may include a flexible collapsible collection bag, a sturdy container, a semi-rigid container, and a soft casing. The material used to fabricate the collection container 22 can be any material which is suitable for the purpose of preventing leaks. For example, the collection container 22 can be PVC, polyurethane, etc. In some embodiments, the collection container 22 may be constructed of a urethane material which can be molded to the upper edge portion 14 on the first end 18 and the outlet port 42 on the second end 46. Depending on the desired application, manner for storing, and/or method of use, the collection container 22 may be pliable, flexible, collapsible, stiff, hard, or rigid. In some embodiments, the collection container 22 may be fabricated using the same material as the upper edge portion 14 and the outlet port 42.

Figure 5:
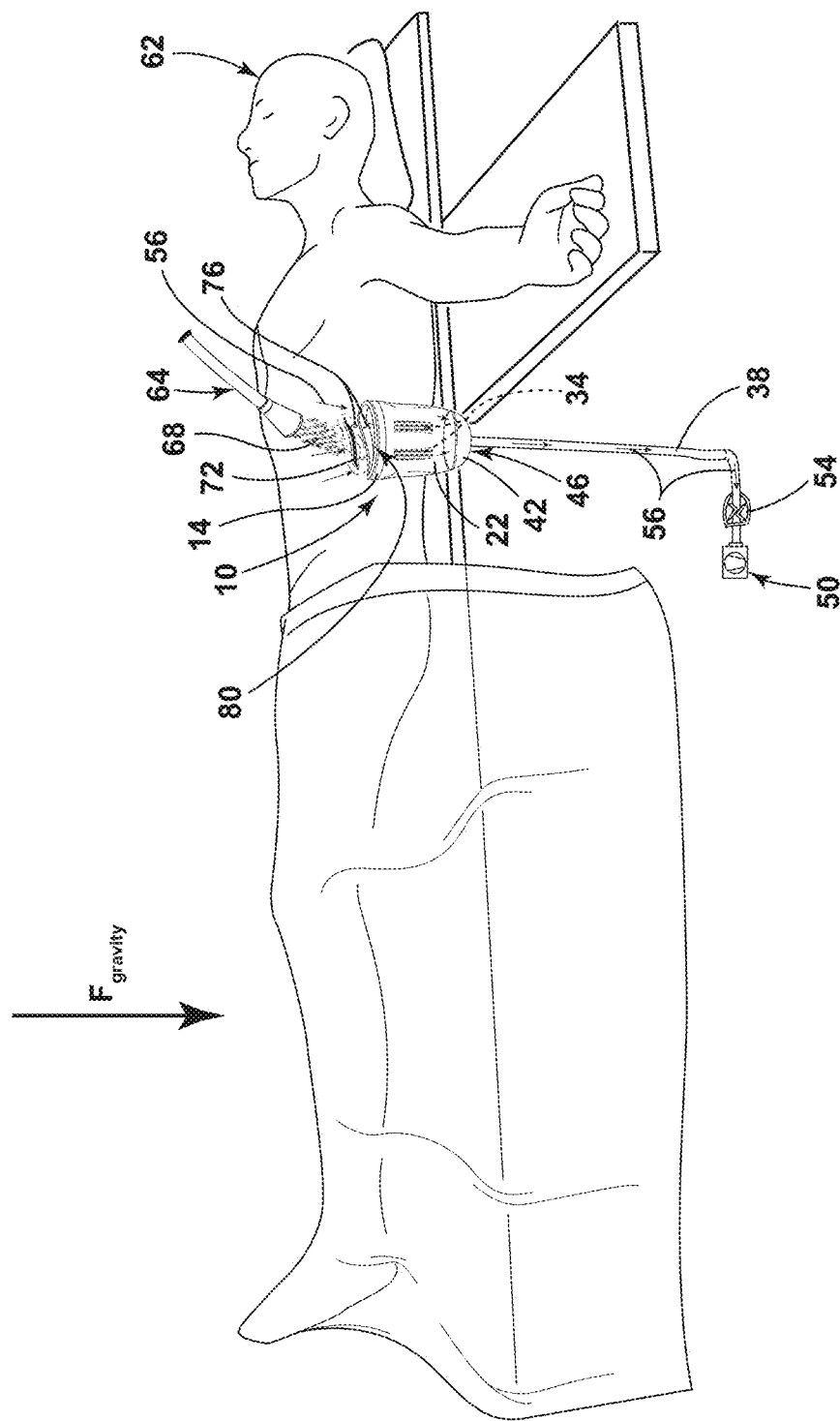
FIG. 5 is a side perspective view illustrating a spraying device and a fluid collection device attached to a patient's body.

Referring now to FIG. 5, the fluid collection device 10 is shown on the patient's body 62 below the laceration 72 or operating incision. The pressurized spraying means 64 applies the fluid 68 to the laceration 72 to generate the contaminated fluids 76 that flow downward with gravity into the open top end 30 of the fluid collection device 10. The contaminated fluids 76 will collect in the collection container 22 and pool into the outlet port 42 where the contaminated fluids 76 may be removed from the interior volume 58 through the application of the vacuum 56 through the vacuum hose 38 by the vacuum source 50. The pinch clip 54 can be activated to cut the vacuum to the fluid collection device 10 as needed.

The pressurized spraying means 64 is not meant to be limiting and may include any device that can project the fluid 68 onto, in, or around the laceration 72 on a patient's body 62. For example, in some embodiments, the pressurized spraying means 64 may be a squirt bottle, a water hose, a pressurized tank system, a faucet, a pump system, or any other device that can apply fluid to a site. The fluid 68 can be, for example, water or any water/saline based fluid that may have medications or antibacterial components. In some embodiments, the pressurized spraying means 64 may be coupled to the fluid collection device 10 or may be a separate standalone device. In some embodiments, a pressurized spraying means 64 is used to irrigate and/or debride the laceration 72 with the fluid 68. In some embodiments, the pressurized spraying means 64 may be a pressurized spraying attachment or separate device that may be attached or coupled to the fluid collection device 10.

The fluid collection device 10 may come in a variety of different sizes (e.g., small, medium, large, extra large) depending on the location, type, and severity of the laceration 72 and/or injury. The upper edge portion 14 may have a series of different diameters or cross section and both the collection container 22 and the outlet port 42 may be appropriately sized to couple together the pieces of the fluid collection device 10.

Figure 6:
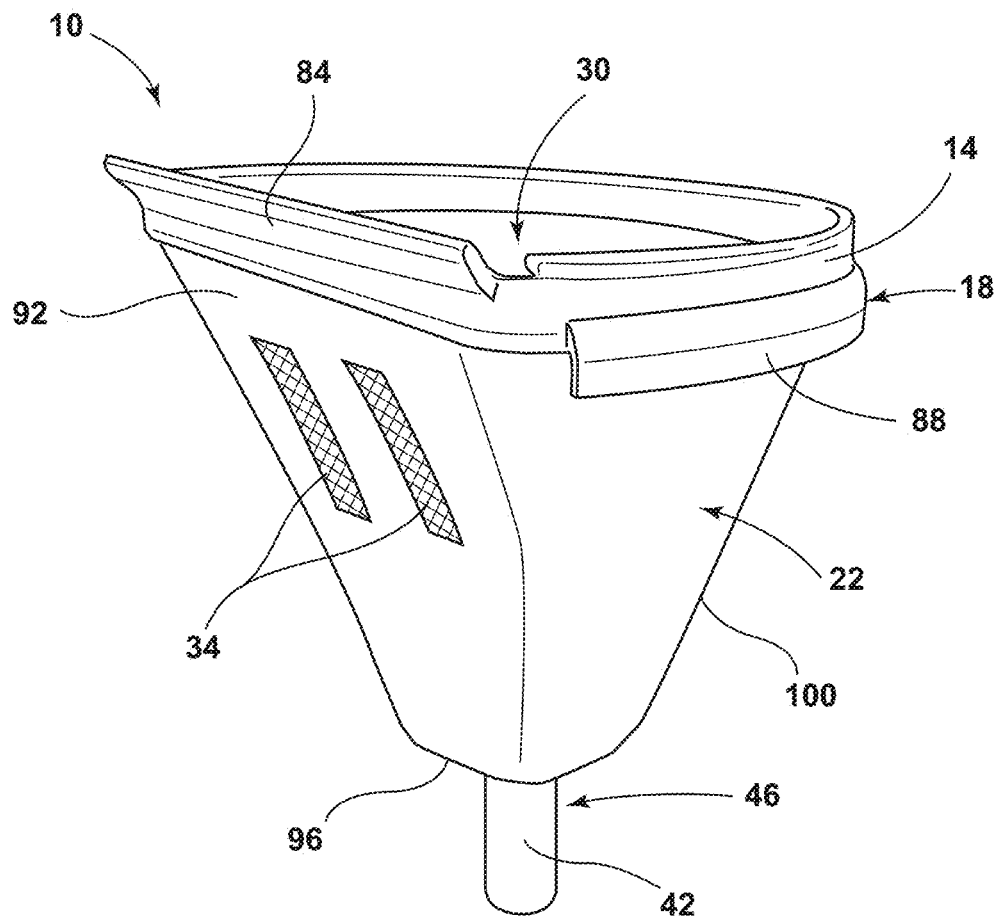
FIG. 6 is a rear isometric view of a fluid collection device according to one aspect of the current invention.
Figure 7:
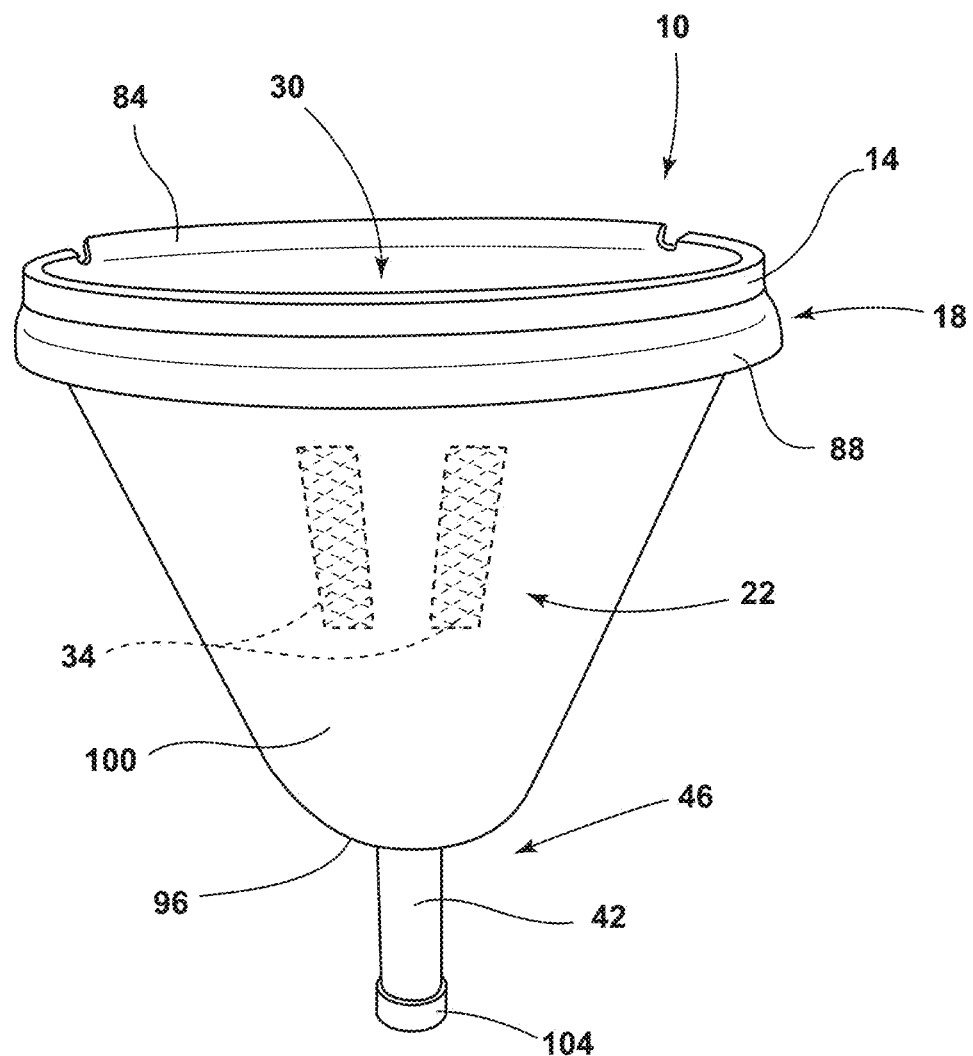
FIG. 7 is a front view of the fluid collection device as shown in FIG. 6.
Figure 8:
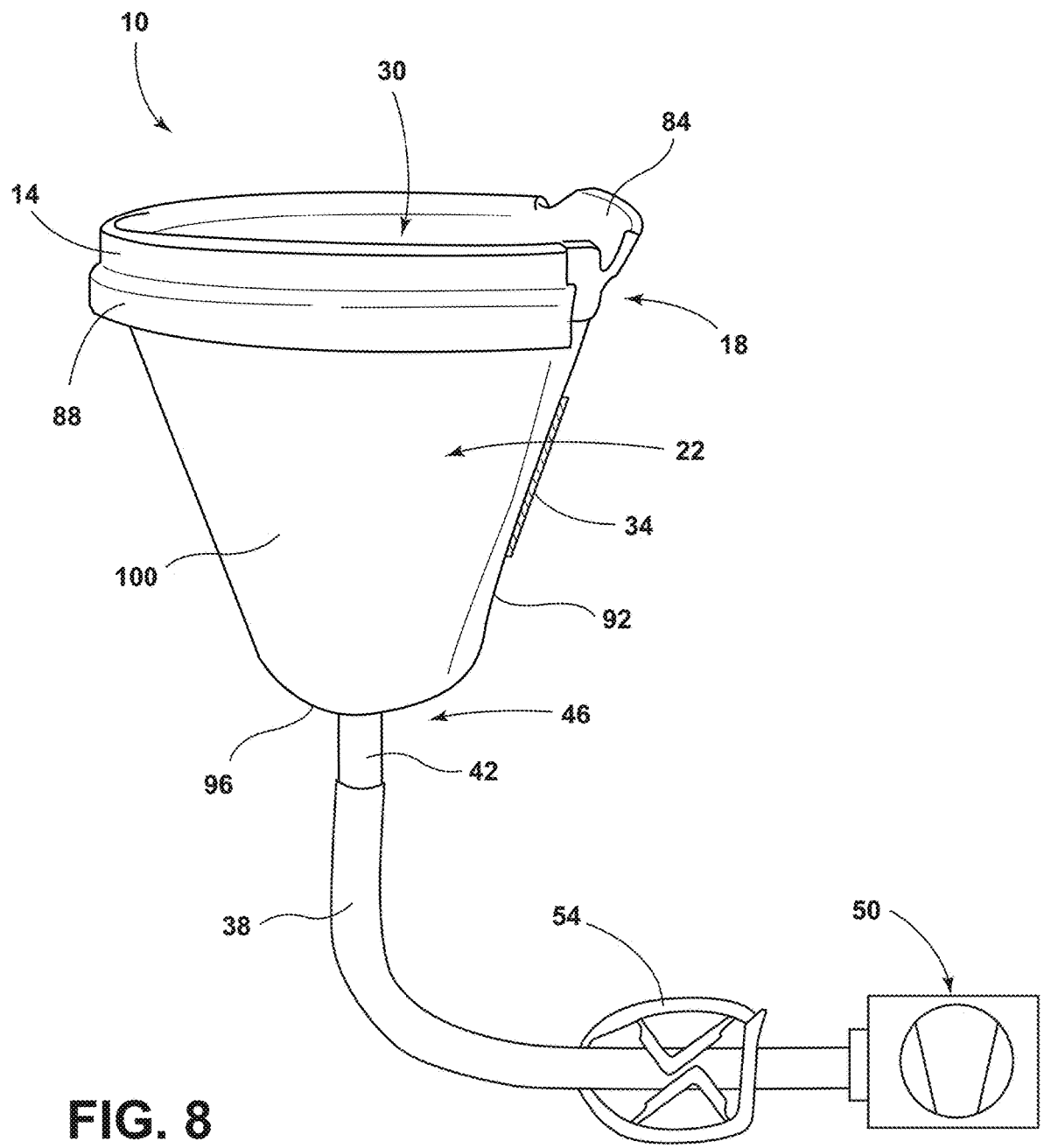
FIG. 8 is a side view of the fluid collection device as shown in FIG. 6.
Figure 9:
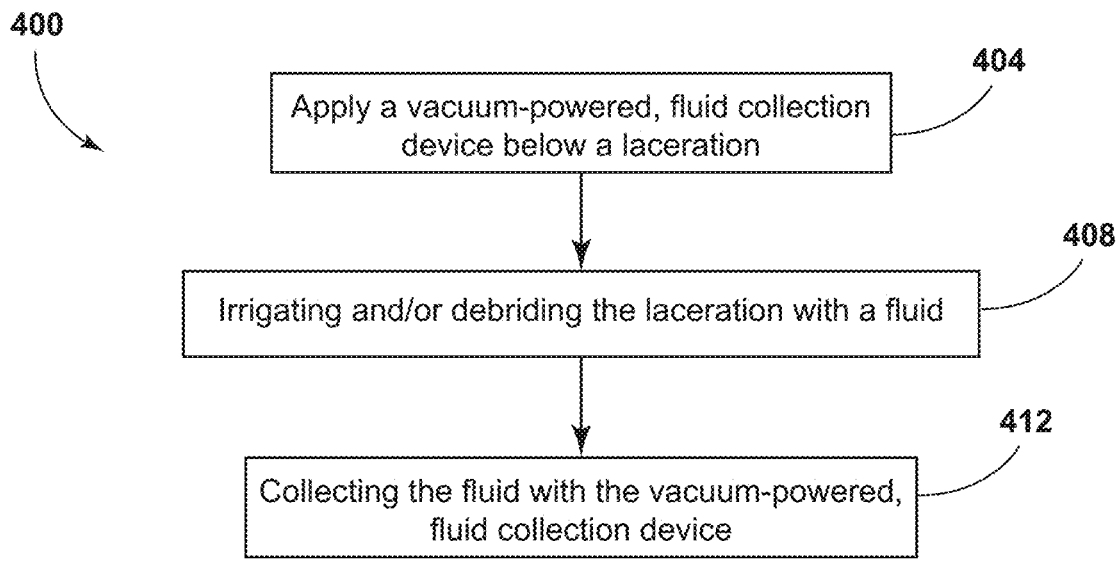
FIG. 9 is a flow diagram of a method for irrigating and draining the laceration.
Figure 10:
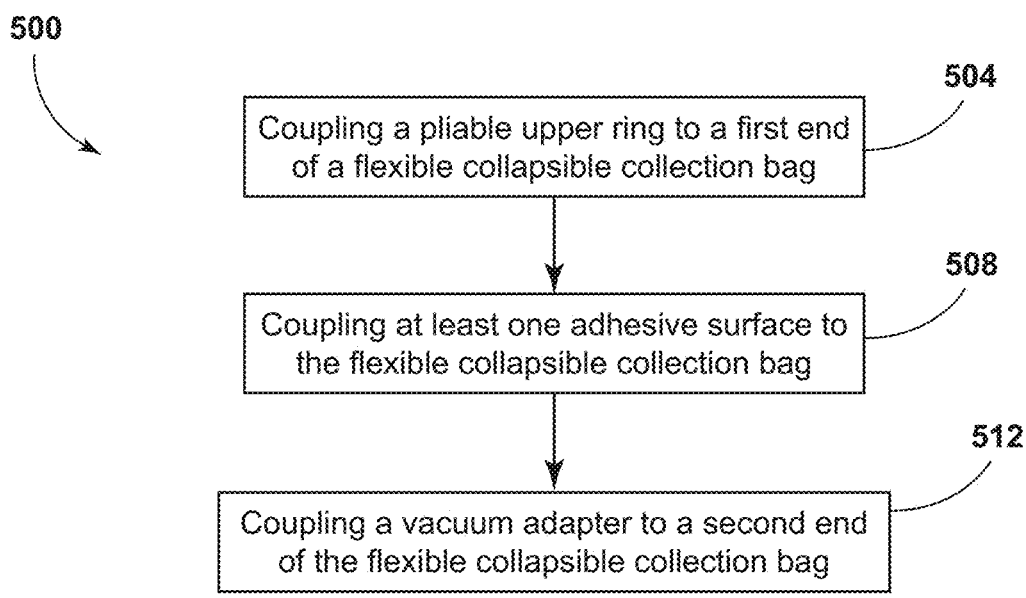
FIG. 10 is a flow diagram of a method for making a fluid collection device.

Referring now to FIGS. 6-8, the fluid collection device 10 includes the upper edge portion 14 having the first end 18 of the collection container 22 having the outer surface 26 where the upper edge portion 14 defines the open top end 30. At least one adhesive surface 34 may be attached to a rear surface 92 of the collection container 22. The second end 46 of the collection container 22 may include the outlet port 42. In some aspects, as shown in FIG. 8, the outlet port 42 may be placed in communication with the vacuum source 50 using the vacuum hose 38 and the pinch clip 54. The collection container 22 may also include a bottom surface 96 and/or a front surface 100. In some aspects, when the vacuum source 50 is not available to be used with the fluid collection device 10, the cap 104 may be used to block the outlet port 42 so contaminated fluids 76 (FIG. 4) may be gathered and held in the collection container 22.

Still referring to FIGS. 6-8, a lip 84 is shown coupled or molded to the upper edge portion 14. The lip 84 can be formed to a shape of the patient's body directly below the laceration 72. A ridge 88 is shown coupled or molded with the upper edge portion 14. The ridge 88 is configured to couple a fastener to hold the fluid collection device 10 to the patient's body 62. In some embodiments, the fastener may include, for example, a rubber band, a bandage, a strap, a belt, or other fastener apparent to one skilled in the art. In some embodiments, the lip 84 may be fabricated using a softer material (e.g., silicone, siloxane, or other elastomeric polymer) or the same material as the polymeric material used to fabricate the upper edge portion 14 and/or collection container 22. In other embodiments, the ridge 88 may be fabricated using a harder material or the same material as the polymeric material used to fabricate the collection container 22. In some embodiments, the lip 84 is positioned above the rear surface 92 of the collection container 22 and the ridge 88 is positioned above the front surface 100 of the collection container 22.

Referring now to FIGS. 1-9, a method 400 for irrigating and draining the laceration 72 includes applying the fluid collection device 10 directly below the laceration 72 (step 404). The fluid collection device 10 has the upper edge portion 14 coupled to the first end 18 of the collection container 22. The collection container 22 has the outer surface 26 where the upper edge portion 14 defines the open top end 30. At least one adhesive surface 34 may be coupled to the outer surface 26 of the collection container 22. The second end 46 defines the outlet port 42 connecting the vacuum source 50 to the outlet port 42 to define the vacuum region 80 proximate the upper edge portion 14 and around the laceration 72. Next, the laceration 72 is irrigated with the fluid 68 to remove dirt, contaminants, and/or dead tissue (step 408). Lastly, the fluid 68 is collected by the fluid collection device 10 when the contaminated fluids 76 flow down into the device via vacuum 56 and/or gravity and are removed from the device through the application of the vacuum 56 by the vacuum source 50 (step 412).

The adhesive properties of the fluid collection device 10 imparted by the at least one adhesive surface 34 helps conform it to the patient's body 62 allowing the fluid collection device 10 to be placed in a hands-free configuration such that the medical staff or caregiver does not need to hold a collection pan against the patient's body 62 during the procedure. The patient may be a human, cat, dog, horse, or any other living being that may have lacerations, incisions, sores, or other wounds that may need irrigation or debridement.

Referring now to FIGS. 1-8 and 10, the process 500 for making the fluid collection device 10 begins by coupling or molding the upper edge portion 14 to the first end 18 of the collection container 22 having the outer surface 26 (step 504). The upper edge portion 14 defines the open top end 30 where the contaminated fluids 76 will enter the fluid collection device 10. Next, at least one adhesive surface 34 will be coupled to the outer surface 26 and/or rear surface 92 of the collection container 22 (step 508). A outlet port 42 is then coupled to the second end 46 of the collection container 22 (step 512), wherein the outlet port 42 may be a rigid member that partially maintains the collection container 22 in an open configuration to place an area defined by the upper edge portion 14 in communication with the outlet port 42.

In some embodiments, the fluid collection device 10 can additionally be collapsed by folding the first end 18 and the second end 46 into each other to form the compacted structure. In other embodiments, the fluid collection device 10 can be stacked in order to, for example, store, ship, stock, or make available a plurality of fluid collection devices 10 for a given application.

It will be understood by one having ordinary skill in the art that construction of the described device and other components is not limited to any specific material. Other exemplary embodiments of the device disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

The above description is considered that of the illustrated embodiments only. Modifications of the device will occur to those skilled in the art and to those who make or use the device. Therefore, it is understood that the embodiments shown in the drawings and devices or methods described above are merely for illustrative purposes and not intended to limit the scope of the device, which is defined by the following claims as interpreted according to the principles of patent law, including the Doctrine of Equivalents.

The invention claimed is:

1. A fluid collection device comprising:
 a pliable upper edge portion coupled to a first end of a collection container having an outer surface wherein the pliable upper edge portion defines an open top end;
 a pliable lip continuously extending along a portion of the pliable upper edge portion and a ridge coupled to the pliable upper edge portion;
 at least one fastening device coupled to the collection container; and
 a second end of the collection container having an outlet port, wherein the outlet port is adapted to be placed in communication with a vacuum source.

2. The fluid collection device of claim 1, wherein the first end and the second end of the collection container can fold towards each other to collapse into a compact structure to define a flat-storage position.

3. The fluid collection device of claim 1, wherein the at least one fastening device is configured to couple to a patient's body directly below a laceration to define a vacuum region around the laceration.

4. The fluid collection device of claim 1, wherein the pliable upper edge portion includes a lip that is configured to be formed to a shape of a patient's body directly below a laceration.

5. The fluid collection device of claim 1, wherein the vacuum source further defines a vacuum region and selectively provides a suction force to assist in removal of a fluid collected in the collection container through a vacuum hose.

6. The fluid collection device of claim 1, wherein the pliable upper edge portion comprises a moldable thermopolymer.

7. The fluid collection device of claim 1, wherein the at least one fastening device is one or more elastic bands.

8. The fluid collection device of claim 1, further comprising a pressurized spraying means used to irrigate and/or debride a laceration with a fluid.

9. A fluid collection device comprising:
 a collection container having an upper edge portion positioned at a first end wherein the upper edge portion defines an open top end;
 a pliable lip continuously extending along a portion of the pliable upper edge and a ridge coupled to the upper edge portion; and
 a second end of the collection container having an outlet port, wherein the collection container is tapered from the first end to the second end, the second end having a narrow width relative to the first end;
 wherein the pliable lip is configured to be molded to a shape of a patient's body directly below a laceration and the ridge is configured to couple a fastener to hold the fluid collection device to the patient's body, wherein the pliable lip includes a material configured to retain the molded shape of the pliable lip during use.

10. The fluid collection device of claim 9, further comprising:
 at least one fastening device coupled to the collection container.

11. The fluid collection device of claim 9, wherein the outlet port is adapted to be placed in communication with a vacuum source.

12. The fluid collection device of claim 9, wherein the pliable lip, ridge, upper edge portion, outlet port, and collection container are all a single molded article.

13. The fluid collection device of claim 9, further comprising a pressurized spraying means used to irrigate and/or debride the laceration with a fluid.

14. A method for irrigating and draining a laceration comprising steps of:
 applying a fluid collection device directly below the laceration wherein the fluid collection device includes:
  a pliable upper edge portion coupled to a first end of a collection container having an outer surface wherein the pliable upper edge portion defines an open top end;
  at least one fastening device coupled to the outer surface of the collection container; and
  a second end defining an outlet port configured to connect a vacuum source to the outlet port to define a vacuum region proximate the pliable upper edge portion and beneath the laceration, wherein the collection container is tapered from the first end to the second end;
 molding the pliable upper edge portion to a shape of a patient's body below the laceration, wherein the pliable upper edge portion includes a material configured to maintain the molded shape of the pliable upper edge portion during use;
 irrigating and/or debriding the laceration with a fluid to remove dirt, contaminants, and/or dead tissue; and
 collecting the fluid with the fluid collection device using the vacuum source and/or gravity.

15. The method for irrigating and draining a laceration of claim 14, wherein the at least one fastening device is coupled to a patient's body directly below the laceration.

16. The method for irrigating and draining a laceration of claim 14, wherein the pliable upper edge portion can be formed to a patient's body directly below the laceration.

17. The method for irrigating and draining a laceration of claim 14, wherein the vacuum source assists in removal of the fluid collected in the collection container through a vacuum hose.

18. The method for irrigating and draining a laceration of claim 14, wherein the irrigating and/or debriding step is performed with a pressurized spraying means.

19. The method for irrigating and draining a laceration of claim 14, wherein the vacuum source further defines a vacuum region and selectively provides a suction force to assist in removal of a fluid collected in the collection container through a vacuum hose.

20. The method of irrigating and draining a laceration of claim 14 further comprising the step of:
 removing the fluid collection device and folding the first end and the second ends of the collection container towards each other to collapse into a compact structure to define a flat-storage position.

* * * * *